United States Patent
Saunois et al.

(10) Patent No.: US 11,026,441 B2
(45) Date of Patent: Jun. 8, 2021

(54) AVOCADO FLESH AND/OR SKIN EXTRACT RICH IN POLYPHENOLS AND COSMETIC, DERMATOLOGICAL AND NUTRACEUTICAL COMPOSITIONS COMPRISING SAME

(71) Applicant: Laboratoires Expanscience, Paris la Défense (FR)

(72) Inventors: Alex Saunois, Dreux (FR); Caroline Baudouin, Rambouillet (FR); Sophie Leclere-Bienfait, Dreux (FR); Sebastien Garnier, Le Rouret (FR); Philippe Msika, Versailles (FR)

(73) Assignee: LABORATOIRES EXPANSCIENCE, Paris la Defense (FR)

( * ) Notice: Subject to any disclaimer, the term of this patent is extended or adjusted under 35 U.S.C. 154(b) by 0 days.

(21) Appl. No.: 16/117,511

(22) Filed: Aug. 30, 2018

(65) Prior Publication Data

US 2018/0369193 A1 Dec. 27, 2018

Related U.S. Application Data

(62) Division of application No. 13/824,627, filed as application No. PCT/EP2011/073832 on Dec. 22, 2011.

(30) Foreign Application Priority Data

Dec. 22, 2010 (FR) ....................... 1061055

(51) Int. Cl.
| | |
|---|---|
| *A61K 36/54* | (2006.01) |
| *A23L 19/00* | (2016.01) |
| *A61Q 17/00* | (2006.01) |
| *A61Q 19/00* | (2006.01) |
| *A61Q 19/02* | (2006.01) |
| *A61Q 19/08* | (2006.01) |
| *A23L 33/105* | (2016.01) |
| *A61K 9/00* | (2006.01) |
| *A61K 8/9789* | (2017.01) |
| *A61K 8/9794* | (2017.01) |
| *A61K 8/49* | (2006.01) |
| *A61K 31/353* | (2006.01) |
| *A61K 45/06* | (2006.01) |
| *A61Q 5/12* | (2006.01) |
| *A61Q 17/04* | (2006.01) |

(52) U.S. Cl.
CPC .............. *A23L 19/07* (2016.08); *A23L 19/09* (2016.08); *A23L 33/105* (2016.08); *A61K 8/498* (2013.01); *A61K 8/9789* (2017.08); *A61K 8/9794* (2017.08); *A61K 9/0014* (2013.01); *A61K 31/353* (2013.01); *A61K 36/54* (2013.01); *A61K 45/06* (2013.01); *A61Q 5/12* (2013.01); *A61Q 17/00* (2013.01); *A61Q 17/04* (2013.01); *A61Q 19/00* (2013.01); *A61Q 19/005* (2013.01); *A61Q 19/02* (2013.01); *A61Q 19/08* (2013.01); *A23V 2002/00* (2013.01); *A61K 2800/92* (2013.01)

(58) Field of Classification Search
CPC .... A61K 36/54; A61K 9/0014; A61K 8/9789; A61K 8/9794; A61K 8/498; A61K 31/353; A61K 45/06; A61K 2800/92; A61Q 17/00; A61Q 17/04; A61Q 19/005; A61Q 19/02; A61Q 19/08; A61Q 19/00; A61Q 5/12; A23L 19/07; A23L 19/09; A23L 33/105; A23V 2002/00; A23V 2200/318; A23V 2250/21
See application file for complete search history.

(56) References Cited

U.S. PATENT DOCUMENTS

| | | | | |
|---|---|---|---|---|
| 6,610,320 | B2 * | 8/2003 | Schmitz | ............... A23G 1/30 424/440 |
| 2008/0194476 | A1 | 8/2008 | Piccirilli et al. | |
| 2008/0305059 | A1 * | 12/2008 | Chaudhuri | ............. A61K 8/347 424/62 |
| 2010/0136144 | A1 * | 6/2010 | Msika | ..................... A61P 33/00 514/1.1 |

FOREIGN PATENT DOCUMENTS

| | | |
|---|---|---|
| FR | 2928263 A1 | 9/2009 |
| FR | 2945445 B1 | 12/2012 |
| JP | 2001322943 A | 11/2001 |
| JP | 2004115466 A | 4/2004 |
| JP | 2004123622 A | 4/2004 |
| MX | JL05000056 A * | 6/2007 |

(Continued)

OTHER PUBLICATIONS

Ramirez-Martinez et al., "Phenolic Compounds in Frozen Avocados", 1973, J. Sci. Fd Agric., vol. 24, pp. 219-225. (Year: 1973).*

(Continued)

*Primary Examiner* — Ali Soroush
(74) *Attorney, Agent, or Firm* — Rouget R. Henschel; Potomac Law Group, PLLC

(57) ABSTRACT

The invention relates to an avocado extract rich in polyphenols, containing at least 10% by weight of polyphenols, expressed in gallic acid equivalent relative to the dry extract obtained, wherein said polyphenols contain procyanidins, cafeic acid and cafeic acid derivatives, typically in a proportion of at least 70% by weight, expressed in gallic acid equivalent relative to the total polyphenol content by weight. The invention also relates to a composition comprising an extract according to the invention as active agent and a suitable excipient. The invention also relates to such a composition or such an extract for use thereof in preventing or treating disorders or pathological conditions of the skin, the mucous membranes or the superficial body growths. Finally, the invention relates to a cosmetic care process for the skin, the superficial body growths or the mucous membranes, with a view to improving the condition thereof or the appearance thereof, which consists in administering such a composition or such an extract.

12 Claims, No Drawings

(56) References Cited

FOREIGN PATENT DOCUMENTS

| WO | 2005105123 A1 | | 11/2005 | | |
|---|---|---|---|---|---|
| WO | WO-2005105123 A1 | * | 11/2005 | ........... | A61K 31/198 |
| WO | WO-2005115421 A1 | * | 12/2005 | .............. | A61P 11/02 |
| WO | 2010100341 A1 | | 9/2010 | | |

OTHER PUBLICATIONS

Soong et al., Antioxidant activity and phenolic content of selected fruit seeds, Dec. 2004, Food Chemistry, vol. 88, pp. 411-417 (Year: 2004).*

Hirasawa et al., "Quantification and functional analysis of dietary fiber and polyphenols in avocado," Nippon Shokuhin Kagaku Kogaku Kaishi, vol. 55, No. 3, pp. 95-101, 2008.

Martinez et al., "Natural Antioxidants Preserve the Lipid Oxidative Stability of Minimally Processed Avocado Puree," Journal of Food Science, vol. 70, No. 5, pp. s325-s329, Jun. 2005.

Prabha et al., "Polyphenols of Avocado (*Persea americana*) and their endogeneous oxidation," Journal of Food Science and Technology, vol. 17, No. 5, pp. 215-217, Jan. 1980.

Ramirez-Martinez et al., "Phenolic Compounds in Frozen Avocados," J. Sci. Fd. Agric., vol. 24, pp. 219-225, 1973.

Stafford et al., "Procyanidins (Condensed Tannins) in Green Cell Suspension Cultures of Douglas Fir Compared with Those in Strawberry and Avocado Leaves by Means of C(18)-Reversed-phase Chromatography," Plant Physiology, vol. 66, No. 6, pp. 1085-1090, Dec. 1980.

Wang et al., "Antioxidant capacities, procyanidins and pigments in avocados of different strains and cultivars," Food Chemistry, vol. 122, pp. 1193-1198, 2010.

* cited by examiner

AVOCADO FLESH AND/OR SKIN EXTRACT RICH IN POLYPHENOLS AND COSMETIC, DERMATOLOGICAL AND NUTRACEUTICAL COMPOSITIONS COMPRISING SAME

This application is a divisional of U.S. patent application Ser. No. 13/824,627, filed Mar. 18, 2013, which is a U.S. national stage of PCT/EP2011/073832, filed Dec. 22, 2011, which claims priority to French Patent Application No. 1061055, filed Dec. 22, 2010, all of which are incorporated herein by reference in their entirety.

The invention relates to an extract of avocado fruit, notably avocado flesh and/or skin, rich in polyphenols, and to cosmetic, pharmaceutical, dermatological and nutraceutical compositions including such an extract and optionally a suitable carrier.

The invention also has as an object a method for extracting an avocado extract rich in polyphenols, as well as the extract likely to be obtained by said method.

The invention also relates to such a composition or such an extract for use thereof in the prevention or treatment of disorders or pathologies of the skin, mucous membranes or appendages. Finally, the invention relates to a cosmetic care method for the skin, appendages or mucous membranes, in order to improve the condition or appearance thereof, consisting of administering such a composition or such an extract.

The avocado tree (*Persea americana* or *Persea gratissima*) belongs to the family Lauraceae.

There is a great diversity of avocado varieties. Among the most widespread, mention may be made of the Hass, Fuerte, Ettinger, Bacon, Nabal, Ananheim, Lula, Reed, Zutano, Quenn, Criola Selva, Mexicana Canta, Tegion Dschang, Hall, Booth, Peterson and Collinson Redn varieties. Particularly, the Hass, Fuerte, Ettinger and Bacon varieties will be selected, and more advantageously the Hass and Fuerte varieties. The weight of the fruits may vary from 50 g to more than 1 kg. The fruit consists of 10 to 20% seed, 7 to 15% integument and 65 to 80% flesh. The skin is of variable thickness, texture and color, smooth to rough, in general green but may become brown, purplish to black.

The flesh is of variable flavor and color and is on average composed of:

TABLE 1

Composition of avocado flesh; *Wei Wang, Food Chemistry, 122: 1193-1198 (2010)

| | |
|---|---|
| Water | 70-85% |
| Proteins | 1.5-4.5% |
| Lipids | 12-23% |
| Sugars | 1.5-5% |
| Fibers | 1.1-1.6% |
| Polyphenols | Between 0.06 and 0.5% in fresh flesh Highly variable = (varieties) |

The flesh of the avocado is widely used by South American population to give the hair shine. Topical applications of avocado flesh on the skin are also very common for its antioxidant and nutritive activity, related to the nature of the lipids of which it is composed (fatty acids and unsaponifiable fraction-vitamin E).

The fruits, in particular their flesh, are commonly used in home remedies in the tropics. The fruits are very rich in vitamins A, B, C, D, E and K and are recommended for diabetics. The flesh is also acaricidal (and vermifugal), aphrodisiac and tonic. It is used in South America in poultices to treat boils and whitlow.

It has been shown that a high consumption of avocados has an effect on blood cholesterol levels. In particular, after 7 days of an avocado-rich diet, patients with hypercholesterolemia saw their total cholesterol levels decrease by 17%. These subjects also showed a 22% decrease in (bad) LDL cholesterol levels and triglycerides, and an 11% increase in (good) HDL cholesterol. Its monounsaturated fatty acids are excellent for cardiovascular health and good blood cholesterol (HDL). Moreover, the avocado is a very good source of fibers (soluble and insoluble) and antioxidants.

The term "polyphenols" refers to a vast family of molecules, widespread in the plant world, characterized by the presence of one or more phenolic nuclei, notably comprising the following subfamilies:

phenolic acids (cinnamic and benzoic);

flavonoids, near-universal plant pigments, responsible for the colors of flowers, fruits and sometimes leaves. Anthocyans are members of this family (blue to violet in color, passing through red);

quinones and anthraquinones and certain derived condensed forms; and more complex and polymerized forms: hydrolysable tannins derived from gallic acid and ellagic acid; condensed tannins derived from catechic acid, OPC or proanthocyanidols.

These molecules are known for their numerous biological activities (antioxidant, anti-inflammatory, antibacterial) and are used in the fields of pharmacy, cosmetics and nutrition/dietary supplements as a function of certain specific structures.

Polyphenols are widely distributed in numerous families of the higher plant kingdom because they are often essential to their survival, namely protection against various external attacks (UV rays, drought, microorganisms, etc.).

Among the most widespread and used polyphenols, mention may be made of polyphenols from Lea (*Camellia sinensis*), grape (*Vitis vinifera*), cocoa (*Theobroma cacao*). The application FR 2 928 263 describes compositions including a combination of plant polyphenols (apple polyphenols are described in particular) and plant sugars. The polyphenols sought are polymeric polyphenols, and in particular procyanidins and prodelphinidins. The avocado is not cited as a source of sugars.

The inventors have discovered that polyphenol-rich extracts of avocado (*Persea gratissima* or *americana*) have cosmetic, dermatological, pharmaceutical and nutraceutical properties, in particular cosmetic and dermatological properties, never described to date. In particular, it is the first time that polyphenol-rich extracts of avocado have been used as such, for their specific properties.

The objects of the invention are in particular:

a polyphenol-rich extract of avocado fruit, containing at least 10% by weight of polyphenols, expressed in gallic acid equivalents in relation to the dry extract obtained, said polyphenols advantageously being procyanidins, caffeic acid and derivatives of caffeic acid, typically in a proportion of at least 70% by weight expressed in gallic acid equivalents in relation to the total polyphenols content by weight. In particular, the extract contains 10 to 30% by weight of polyphenols expressed in gallic acid equivalents in relation to the weight of the dry extract. The proportions of procyanidins, caffeic acid and derivatives of caffeic acid in said polyphenols are advantageously at least 80% by weight expressed in gallic acid equivalents in relation to the total polyphenols content by weight.

The procyanidins are advantageously selected from the group composed of B-type procyanidin dimers, A- and B-type procyanidin trimers and A- and B-type procyanidin tetramers.

The polyphenols contained in this extract advantageously contain at least 30% by weight of procyanidins, expressed in gallic acid equivalents in relation to the total polyphenols content by weight.

The polyphenols contained in this extract advantageously contain caffeic acid and derivatives thereof, typically in a proportion of at least 30% by weight, expressed in gallic acid equivalents in relation to the total polyphenols content by weight.

The extract advantageously further includes at least 10%, advantageously from 10 to 60% of avocado sugars, said sugars containing at least D-mannoheptulose and/or perseitol, with percentages being expressed by weight in relation to the total weight of the dry extract.

The extract is advantageously obtained by extraction of the avocado fruit, advantageously by extraction of avocado fruits that first have been dried, under gentle conditions, and then delipidated.

In one advantageous variant, it is obtained by solid-liquid extraction of part of the avocado fruit in an aqueous and/or alcoholic and/or glycolic and/or glycerolic solvent. The solvent is advantageously selected from the group composed of water, ethanol, glycerol or a glycol such as propanediol, and mixtures thereof, such as binary mixtures, in proportions between 0 and 100% of water in relation to other solvents.

a composition including as active agent an extract of the invention and, advantageously a suitable carrier. In particular, the composition is a cosmetic, pharmaceutical, dermatological or nutraceutical composition.

The composition advantageously further includes another active agent, in particular selected from the group composed of emollients, moisturizing active agents, keratoregulators, keratolytics, healing agents and/or agents that restructure the cutaneous barrier, PPAR, RXR or LXR agonists, sebum-regulating agents, anti-irritation and/or anti-inflammatory and/or soothing agents, antioxidant agents, anti-aging agents, depigmenting or hypopigmenting agents, pigmenting agents, lipolytic or lipogenesis inhibitor agents or anti-cellulitis or slimming agents, organic or mineral sun screens and filters (pigmentary or ultrafine), antifungal compounds, preservatives, antibacterial agents, prebiotics and probiotics, antibiotics, and immunomodulators.

The composition advantageously includes as another active agent an agent useful in the treatment of acne, in particular selected from the group comprised of 5-alpha reductase inhibitors, zinc (and gluconate, salicylate salts thereof, and pyroglutamic acid), spironolactone, linoleic acid, antibiotics, benzoyl peroxide, azelaic acid, vitamin PP, vitamin B3, cycl ins, extracts of pumpkin seeds, squash seeds oil and palmetto.

an extract or a composition of the invention to be used as a pharmaceutical, dermatological or cosmetic composition or as a functional food; in particular to be used in the prevention and/or treatment of disorders or pathologies of the skin and/or mucous membranes and/or appendages, more particularly to be used in the prevention and/or treatment of allergic, inflammatory, irritative reactions or pathologies, or disorders of the barrier or homeostasis of the skin, or vascular disorders, or as a depigmenting or healing agent.

a cosmetic care method for the skin and/or appendages and/or mucous membranes, with a view to improving the condition and/or appearance thereof, consisting of administering a composition or an extract of the invention.

The expression "polyphenol-rich extract of avocado" refers to an extract obtained by methods making it possible to concentrate the polyphenols potentially present in the avocado in such a way that this extract contains at least 10% by weight of polyphenols, expressed in gallic acid equivalents in relation to the weight of the dry extract. According to one advantageous variant of the invention, the extract contains 10 to 30% by weight of polyphenols, more advantageously 10 to 20% by weight of polyphenols, expressed in gallic acid equivalents in relation to the dry extract obtained.

The proportion of dry extract in the extract of the invention, expressed by weight in relation to the total weight of the extract, varies from 0.01 to 90%, advantageously from 0.5 to 50%, more advantageously from 0.5 to 15%, even more advantageously from 0.5 to 5%.

The polyphenols contained in this extract contain procyanidins, caffeic acid and derivatives of caffeic acid, in particular esterified derivatives, in a proportion of at least 70%, advantageously at least 80%, more advantageously at least 90%, even more advantageously at least 95c, by weight expressed in gallic acid equivalents in relation to the total polyphenols content by weight.

Procyanidins are oligomers of catechins/epicatechins. Catechin and epicatechin are, respectively, the (+) and (−) optical isomers of the molecule of the following formula (I):

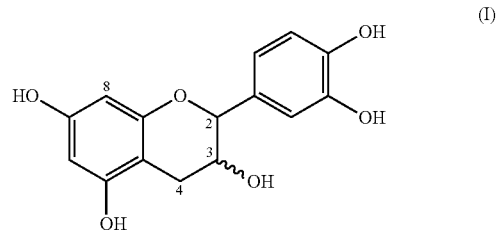 [SMILES: Oc1cc(O)c2c(c1)OC(c1ccc(O)c(O)c1)C(O)C2]

The procyanidins are advantageously B-type procyanidin dimers. Procyanidins of the B-1, B-2, B-3 and B-4 types are dimers composed of two units (+)-catechin and (−)-epicatechin, linked in $C_4$-$C_8$. Procyanidins of the B-5, B-6, B-7 and B-8 types are dimers composed of two units (+)-catechin and (−)-epicatechin, linked in $C_4$-$C_6$.

The procyanidins are more advantageously A and B type procyanidin trimers.

The procyanidins are more advantageously A and B type procyanidin tetramers.

The procyanidins are more advantageously oligomeric or polymeric procyanidins (number of units of catechin or epicatechin >4).

The polyphenols contained in this extract advantageously contain at least 30%, more advantageously at least 50% by weight of procyanidins, expressed in gallic acid equivalents in relation to the total polyphenols content by weight.

The polyphenols contained in this extract advantageously also contain caffeic acid and derivatives thereof in a proportion of at least 20%, more advantageously at least 30% by weight, expressed in gallic acid equivalents in relation to the total polyphenols content by weight.

Caffeic acid has the following formula (II):

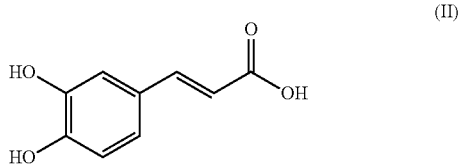 [SMILES: O=C(O)/C=C/c1ccc(O)c(O)c1]

Caffeic acid and its derivative, phenethyl caffeate ester (ester of caffeic acid and 2-phenylethanol), are present in many plants, and in particular in a large quantity in coffee, from which it gets its name. Caffeic acid may be present in esterified form, for example with quinic acid with which it forms chlorogenic acid. Among other esterified forms, mention may be made of caffeoyl tartaric (or caftaric) acid formed with tartaric acid, caffeoyl shikimic acid (formed with shikimic acid), caffeoyl malic acid (formed with malic acid), or esterified with glucose (caffeoyl glucose) or in amide form with putrescine (caffeoyl putrescine).

Other polyphenols may also be present in the extract of the invention but they are, however, a minority. Their content by weight, expressed in gallic acid equivalents in relation to the total polyphenols content by weight, is advantageously less than 30%, more advantageously less than 20%, even more advantageously less than 10%, even more advantageously less than 5%, even more advantageously less than 2%.

According to one advantageous variant of the invention, the extract contains at least 10%, advantageously from 10 to 60%, more advantageously from 10 to 30% of avocado sugars, typically said sugars containing at least D-mannoheptulose and/or perseitol (percentages are expressed by weight in relation to the weight of the dry extract).

In the context of the present invention, the terms "D-mannoheptulose" and "perseitol" also cover the chemical derivatives thereof.

The avocado sugars are mainly D-mannoheptulose, perseitol, sucrose, glucose and fructose. Traces of other sugars may be found, but their content is less than 5% by weight, advantageously less than 2% by weight, in relation to the total weight of avocado sugars.

In the extract of the invention, the total proportion of D-mannoheptulose and/or perseitol in the avocado sugars is advantageously at least 50% by weight in relation to the total sugars content by weight. More advantageously, the total proportion of D-mannoheptulose and/or perseitol in the avocado sugars is from 50 to 98% by weight, more advantageously 55 to 95%; by weight, even more advantageously 60 to 90% by weight, in relation to the total sugars content by weight.

The weight ratio of D-mannoheptulose to perseitol varies advantageously from 1:10 to 10:1.

The extract of the invention advantageously contains 0 to 50% by weight, more advantageously 0 to 20% by weight, even more advantageously 0 to 10; by weight of avocado lipids, with percentages being expressed by weight in relation to the total weight of the dry extract.

The extract of the invention advantageously contains 0 to 60% by weight, advantageously 1 to 30% by weight, even more advantageously 5 to 15% by weigh of avocado proteins, with percentages being expressed by weight in relation to the total weight of the dry extract (Bradford assay).

The extract of the invention is obtained by extraction of a portion of the avocado fruit, preferentially the flesh and/or skin. More particularly, the residual oil cake from the pressing of dried avocado flesh is used. Preferentially, said flesh has been dried beforehand before the lipid extraction.

It is particularly advantageous to use avocado fruits (flesh and/or skin) that first have been dried, under gentle conditions, and then delipidated. Indeed, it has been noted that under such conditions the optimal preservation of polyphenols can be ensured by inactivation of polyphenol oxidase during drying (even extracts containing no polyphenol oxidase can be obtained).

Advantageously, this extract is obtained by solid-liquid extraction of a portion of the avocado fruit in an aqueous and/or alcoholic and/or glycolic and/or glycerolic solvent. The portions of the fruit preferentially selected are dried and/or defatted flesh (oil cake) and/or the skin, more preferentially flesh dried under gentle conditions and then defatted.

The solvent is advantageously selected from the group composed of water, ethanol, glycerol or a glycol such as propanediol, and mixtures thereof, such as binary mixtures, in proportions between 0 and 100% of water in relation to other solvents.

Mainly, binary mixtures of solvents composed of water and a solvent selected from ethanol, glycerol or propanediol are used.

More particularly, between 0.1 and 50% by weight (expressed in relation to the total weight of avocado+solvent) of the dried portion of avocado is introduced into the extraction solvent, and preferentially 10% by weight.

In the presence of ethanol, preferentially a proportion between 30 and 70% of ethanol in water, and advantageously between 50 and 60% of ethanol in water, will be chosen (percentages are expressed by weight of ethanol in relation to the total weight of water+ethanol).

In the presence of glycerol, preferentially a concentration between 40 and 90% of glycerol, and preferentially between 60 and 80%, will be chosen (percentages are expressed by weight of glycerol in relation to the total weight of water+glycerol).

In the presence of glycol, and more particularly of propanediol, preferentially a proportion between 40 and 80%, and advantageously between 50 and 60% of propanediol in relation to water will be chosen (percentages are expressed by weight of propanediol in relation to the total weight of water+propanediol).

The extraction temperature is advantageously between 4 and 100° C., and preferentially between 10 and 60° C., and more particularly between 15 and 30° C.

The extraction period advantageously varies from 30 minutes to 4 hours, more particularly from 30 minutes to 2 hours.

These various extractions may be followed by purification steps of ultrafiltration (10 kDa cut-off, for example), or diafiltration and/or nanofiltration (200 Da cut-off, for example), making it possible to concentrate the polyphenols at the expense of sugars (including the specific $C_7$ avocado sugars, mannoheptulose and perseitol).

The extract obtained following these purification steps advantageously includes 10 to 30% by weight of polyphenols, even more advantageously 10 to 20% by weight of polyphenols, expressed in gallic acid equivalents in relation to the weight of the dry extract.

The sugars content in the extract obtained following these purification steps is advantageously between 5 and 20% by weight, in relation to the weight of the dry extract.

The sugars present in this extract advantageously include 20 to 60% of D-mannoheptulose and/or perseitol, more advantageously 30 to 60% of D-mannoheptulose and/or perseitol, expressed by weight in relation to the total weight of the sugars.

The extract obtained may be provided in liquid form, but also may be dried according to methods known to persons skilled in the art, such as atomization or freeze-drying, for example, with or without a support such as maltodextrin.

The invention also has as an object a method for preparing a polyphenol-rich avocado extract comprising the following sequential steps:
  (a) liquid-phase dispersion in a suitable solvent of avocado fruit (advantageously flesh and/or skin), and advantageously dried defatted flesh (oil cake);
  (b) subjection of the mixture obtained following step (a) to extraction under stirring in an aqueous and/or alcoholic and/or glycolic and/or glycerolic solvent, advantageously a mixture of water and a solvent selected from the group composed of ethanol, glycerol, a glycol (advantageously propanediol) and mixtures thereof, advantageously in a proportion of 60% of these solvents in water;
  (c) centrifugation of the extract obtained following step (b) and then filtration, or filtration directly;
  (d) if the need arises, subjection of the extract obtained following step (c) to an ultrafiltration and/or diafiltration and/or nanofiltration step;
  (e) following step (c) or (d), recovery of the polyphenol-rich extract; and
  (f) optional drying of the extract obtained following step (e) on a support or not.

The extract is advantageously used as an active agent in a cosmetic, pharmaceutical, dermatological or nutraceutical composition, which may include one or more suitable carriers. The composition may further include at least one other active compound in addition to the polyphenol-rich avocado extract. This other compound may be selected from all the compounds and functional equivalents thereof set forth below.

This other compound may be selected in particular from active agents classically used in dermatology, pharmaceuticals, cosmetics or nutraceuticals and known to persons skilled in the art such as emollients, moisturizing active agents, keratoregulators, keratolytics, healing agents and/or agents that restructure the cutaneous barrier, PPAR, RXR or LXR agonists, sebum-regulating agents, anti-irritation and/or anti-inflammatory and/or soothing agents, antioxidant agents, anti-aging agents, depigmenting or hypopigmenting agents, pigmenting agents, lipolytic or lipogenesis inhibitor agents or anti-cellulitis or slimming agents, organic or mineral sun screens and filters (pigmentary or ultrafine), antifungal compounds, preservatives, antibacterial agents, prebiotics and probiotics, antibiotics, and immunomodulators.

More particularly, the healing agents and/or agents that restructure the cutaneous barrier that may be used in combination are advantageously panthenol (vitamin B5), arabinogalactan, zinc oxide, ceramides, cholesterol, squalane and phospholipids.

The sebum-regulating agents that may be used in combination are advantageously selected from the group composed of 5-alpha reductase inhibitors such as Zinc and zinc derivatives (gluconate, salicylate salts thereof and pyroglutamic acid).

The anti-inflammatory and/or anti-irritation and/or soothing agent may be arabinogalactan.

Among hypopigmenting or depigmenting agents, particular mention may be made of N-undecylenoyl-L-phenylalanine (Sepiwhite®).

The sun protection active agents that may be used in combination are advantageously UVB and/or UVA filters or sun screens, such as the mineral and/or organic screens or filters known to persons skilled in the art, who will adapt their choice and their concentrations according to the degree of protection sought.

The preservatives that may be used in combination are, for example, those generally used in cosmetics or nutraceuticals, molecules with antibacterial activity (pseudo-preservatives) such as caprylic derivatives like, for example, capryloyl glycine and glyceryl caprylate; hexanediol, sodium levulinate, and copper and zinc derivatives (gluconate and PCA).

Among the recommended active agents in combination with the extract of the invention, mention may be made of plant extracts, in particular:
  plant oils such as soy oil and/or rapeseed oil, avocado oil (WO2004/012496, WO2004/012752, WO2004/016106, WO2007/057439), lupin oil, advantageously sweet white lupin oil (WO 98/47479), or a mixture of these oils;
  oleodistillates or concentrates of animal or plant oil, notably sunflower, more advantageously linoleic sunflower concentrates, such as the sunflower oil concentrated in unsaponifiables (Soline®) (see the international application WO 01/21150) marketed by Laboratoires Expanscience, oils concentrated in unsaponifiables as the avocado oil, rapeseed oil, corn oil or palm oil, useful notably for their moisturizing and/or emollient, healing and/or cutaneous barrier restructure, anti-inflammatory and/or anti-irritation and/or soothing activity;
  unsaponifiables of plants or of plant oil, advantageously of avocado furans (Avocadofurane®), able to be obtained by the method described in the international application WO 01/21605, unsaponifiables of avocado and/or soy, more particularly a mixture of furanic unsaponifiables of avocado and unsaponifiables of soy, advantageously in a respective ratio of about ⅓-⅔(such as Piascledine®), unsaponifiables of soy (such as obtained according to the method described in the international application WO 01/51596), sterolic unsaponifiables (typically unsaponifiables whose proportion of sterols, methylsterols and triterpene alcohols is between 20 and 95% by weight, preferably 45-65% by weight, in relation to the total weight of the unsaponifiable), phytosterols, esters of sterols and vitamin derivatives, notably useful for their healing and/or restructure of the cutaneous barrier, anti-aging or anti-inflammatory activity;
  peptides or complexes of plant amino acids, in particular of avocado peptides (such as those described in the international application WO2005/105123), lupin peptides (such as those obtained according to the method described in the application WO2005/102259), quinoa peptides (such as those described in the international application WO2008/080974), maca peptides (such as those described in the international application WO2004/112742), fermented or non-fermented soy peptides, rice peptides (such as those described in the international application WO2008/009709), useful notably for their moisturizing and/or emollient activity (avocado), keratoregulating activity (lupin, quinoa), healing and/or cutaneous barrier restructuring activity (maca, quinoa, soy), anti-inflammatory and/or anti-irritation and/or soothing activity (lupin, quinoa), antioxidant activity (avocado), anti-aging activity (lupin, maca) and pigmenting activity (rice);

plant sugars, in particular avocado sugars (such as those described in the application WO2005/115421), useful notably for their keratoregulator, healing and/or cutaneous barrier restructure, anti-inflammatory and/or anti-irritation and/or soothing property; butyl avocadate (5 alpha Avocuta®), 5-alpha reductase inhibitor (see WO 01/52837 and WO 02/06205) typically regulator of the seborrheic secretions found increased in acne and in dandruff;

polyphenol-rich extracts, and more particularly extracts of the above-ground parts of *Gynandropsis gynandra* (FR 1 061 051) and extracts of maca leaves (FR 1 061 047);

lupeol (FR 2 822 821, FR 2 857 596) useful notably to promote healing;

total extract of lupin (such as those described in the international application WO2005/102259), particularly suitable for the treatment of irritations;

extract of *Acacia macrostachya* seeds (FR 0958525), extract of maca leaves (FR 1 061 047), extract of *Schisandra sphenanthera* seeds (FR 0955343 and FR 0955344) and *Vigna unguiculata* seeds (FR 0958529).

Among the recommended active agents in combination with the extract of the invention, mention may be made of oxazolines, in particular those selected from the group comprised of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline, 2-undecyl-4-ethyl-4-hydroxymethyl-1,3-oxazoline, preferably 2-undecyl-4,4-dimethyl-1,3-oxazoline (OX-100 or Cycloceramide®; WO2004050052, WO2004050079 and WO2004112741). They are particularly useful for their anti-inflammatory and/or anti-irritation and/or soothing, antioxidant, depigmenting, immunomodulatory activity.

Among the active agents recommended in combination with the extract of the invention, mention may be made of 5-alpha reductase inhibitors such as butyl avocadate (5 alpha Avocuta®).

All of these combinations include at least one other active compound, in addition to the polyphenol-rich avocado extract, and may include two, three, four or more active compounds as described above.

The composition of the invention may be formulated in the form of various preparations suitable for topical administration, for oral, rectal, vaginal, nasal, auricular or bronchial administration, as well as for parenteral administration.

According to a first variant, the various preparations are suitable for topical administration and notably include creams, emulsions, milks, pomades, lotions, oils, aqueous or water-alcoholic or glycolic solutions, powders, patches, sprays, shampoos, varnishes or any other product for external application.

According to a second variant, the various preparations are suitable for oral administration, with the polyphenol-rich avocado extract incorporated either in a dietary supplement or in a nutraceutical composition. In the context of the present invention, the dietary supplement may be provided in the form of the polyphenol-rich avocado extract as such or in the form of hard or soft plant- or gelatin capsules. Said dietary supplement may thus contain from 10 to 100% by weight of the polyphenol-rich avocado extract.

The composition of the present invention may be incorporated directly and with no other modification in nutraceuticals, diet products, notably hyper-protein products, or beverages by techniques such as mixing, infusion, injection, blending, absorption, kneading and spraying.

The modes of administration, posologies and optimal galenic forms of the compounds and compositions of the invention may be determined according to the criteria generally taken into account in the establishment of a pharmaceutical treatment, in particular a dermatological, cosmetic or veterinary treatment suitable for a patient or an animal, such as for example the age or the body weight of the patient or animal, the severity of the general condition of the patient or animal, tolerance to the treatment, noted side effects and skin type. Depending on the type of administration desired, the active composition and/or compounds of the invention may further include at least one pharmaceutically acceptable carrier, in particular a dermatologically acceptable carrier, or a cosmetically or nutraceutically acceptable carrier. According to the first variant, a carrier suitable for administration by external topical route is used. The composition of the present invention may further include at least one pharmaceutical or cosmetic adjuvant known to persons skilled in the art, selected from thickeners, preservatives, fragrances, colorants, chemical or mineral filters, moisturizing agents, thermal waters, etc.

The composition including a polyphenol-rich avocado extract having the indicated specifications is particularly intended for cosmetic, pharmaceutical or dermatological use. The composition will be formulated advantageously in the form of a preparation suitable for topical administration.

The invention also has as an object the use of a polyphenol-rich avocado extract for the manufacture of a cosmetic, pharmaceutical, dermatological or nutraceutical composition or a functional food.

Advantageously, the composition or extract of the present invention is used in the prevention and/or treatment of disorders or pathologies of the skin and/or mucous membranes and/or appendages.

In particular, the composition or extract of the invention is intended for the prevention and/or treatment of allergic, inflammatory or irritative reactions or pathologies, or disorders of the barrier or homeostasis of the skin, appendages (hair and nails) and/or mucous membranes (gums, periodontium, genital mucosa), whether immature, normal or mature/aged.

The expression "disorders of the barrier of the skin, appendages and/or mucous membranes" refers to disorders intervening at the level of the external layer of the skin.

The expression "disorders of the homeostasis of the skin, appendages and/or mucous membranes" refers to disorders resulting from the processes of cell renewal and equilibrium such as psoriasis, diaper rash, atopic dermatitis, dry skin (xerosis), dehydrated skin and photosensitive skin.

Advantageously, the composition or extract according to the invention may be used for the prevention and/or treatment of reactions, disorders or pathologies of the:

skin, such as rosacea or erythrocouperosis, psoriasis, vascular disorders, diaper rash, atopic dermatitis, eczema, contact dermatitis, irritative dermatitis, allergic dermatitis, seborrheic dermatitis (cradle cap), sensitive skin, reactive skin, pruritus, dry skin (xerosis), dehydrated skin, skin with redness, cutaneous erythema, aged or photoaged skin, photosensitive skin, pigmented skin (melasma, post-inflammatory pigmentation), skin with cellulitis, loose skin, skin with stretch marks, scurf, chapping, bites, cracks, in particular of the breasts, sunburn, inflammations due to rays of all types, irritations by chemical, physical (for example tension stress for pregnant women), bacteriological, fungal or viral, parasitic (lice, scabies, tinea, mites, dermatophytes) or radiological agents, or by a deficit in innate immunity (antimicrobial peptides) or acquired immunity (cellular, humoral, cytokines), and/or mucous membranes such as the gums and periodontium subject to gingivitis (sensitive gums of newborns, problems of hygiene, due the use of tobacco or other products), periodontopathies, or genital mucosa presenting irritations of the external or internal male or female genitalia, and/or epithelial appendages such as the nails (breakable, fragile nails, etc.) and hair (alopecia, dandruff, hirsutism, seborrheic dermatitis, folliculitis) whether immature, normal or mature, presenting in particular disorders of the scalp such as androgenetic, acute, localized, cicatricial and congenital, occipital in infants and areata alopecia (or pelade), due to chemotherapy/radiotherapy or telogen effluvium, anagen effluvium, pilar dystrophy, trichotillomania, tinea or oily or dry dandruff.

The composition or extract of the present invention is also used advantageously in the prevention and/or treatment of vascular disorders, and may be used advantageously in hypopigmentation by decreasing melanin and/or inhibiting tyrosinase, or as a healing agent.

The invention also relates to a cosmetic care method for the skin and/or appendages and/or mucous membranes, with a view to improving the condition and/or appearance thereof, comprising the administration of or consisting of administering a cosmetic composition or an extract of the present invention.

In one embodiment of the cosmetic method of the invention, the intended skin and/or appendages and/or mucous membranes are advantageously those that are sensitive, irritated or damaged by the environment (UV rays, pollution), in particular sensitive skin.

The cosmetic method of the invention is also characterized in that the composition or extract is used as a moisturizing product, or as a chronological or photo-induced anti-aging product in the prevention of aging, and of photo-induced aging, or as a slimming and/or anti-cellulitis product, or as an anti-aging or anti-age spot product.

The expression "moisturizing product" refers to a product that in particular makes it possible to prevent and/or treat disorders of the barrier or homeostasis of the skin, appendages and/or mucous membranes.

The expression "anti-age spot product" refers to a product that makes it possible to reduce spots of pigmentation of the skin and/or appendages and/or mucous membranes.

The expression "slimming and/or anti-cellulitis product" refers to a product that makes it possible to improve the firmness, elasticity or tonicity of the skin, and/or to fight the accumulation of adipose tissue and skin with cellulitis.

EXAMPLE 1

Dried and defatted avocado flesh (oil cake) is suspended under stirring at a concentration of 10% in a 60/40 (w/w) ethanol/water mixture for 1 hour at room temperature. The residual dry matter is separated from the liquid phase by filtration, settling or centrifugation and the liquid phase thus obtained may be filtered using filters of suitable pore size in order to obtain a clear solution. The extract obtained has the following characteristics:

Dry extract: 2.56%

Total sugars (glucose, fructose, mannoheptulose, perseitol; HPLC): 19.5%/dry

Total polyphenols (Folin-Ciocalteu; gallic acid equivalents): 14%/dry

Proteins (Bradford assay): 6.25%/dry.

This extract has anti-radical activity, "in tubo" anti-DPPH activity, for which the half maximal inhibitory concentration ($IC_{50}$) could be determined and is 111 µg of dry extract, which represents 10.6 µg of polyphenols in the reaction medium.

EXAMPLE 2

Dried and defatted avocado flesh (oil cake) is suspended under stirring at a concentration of 10% in a 60/40 (w/w) glycerol/water mixture for 1 hour at room temperature. The residual dry matter is separated from the liquid phase by filtration, settling or centrifugation and the liquid phase thus obtained may be filtered using filters of suitable pore size in order to obtain a clear solution. The extract obtained has the following characteristics:

Dry extract: 3.45%

Total sugars (glucose, fructose, mannoheptulose, perseitol; HPLC): 19%/dry

Total polyphenols (Folin-Ciocalteu; gallic acid equivalents): 12%/dry

Proteins (Bradford assay): 9%/dry.

This extract has anti-radical activity, "in tubo" anti-DPPH activity, for which the half maximal inhibitory concentration ($IC_{50}$) could be determined and is 84 µg of dry extract, which represents 11.85 µg of polyphenols in the reaction medium.

EXAMPLE 3

Dried and defatted avocado flesh (oil cake) is suspended under stirring at a concentration of 10% in a 60/40 (w/w) propanediol/water mixture for 1 hour at room temperature. The residual dry matter is separated from the liquid phase by filtration, settling or centrifugation and the liquid phase thus obtained may be filtered using filters of suitable pore size in order to obtain a clear solution. The extract obtained has the following characteristics:

Dry extract: 2.74%

Total sugars (glucose, fructose, mannoheptulose, perseitol; HPLC): 22%/dry

Total polyphenols (Folin-Ciocalteu; gallic acid equivalents): 16%/dry

Proteins (Bradford assay): 7%/dry.

This extract has anti-radical activity, "in tubo" anti-DPPH activity, for which the half maximal inhibitory concentration ($IC_{50}$) could be determined and is 119.5 µg of dry extract, which represents 18.5 µg of polyphenols in the reaction medium.

EXAMPLE 4: COMPOSITIONS FOR TOPICAL APPLICATION

The inventors present below several compositions for topical application. The polyphenol-rich extracts of avocado (*Persea gratissima* and *americana*) may be incorporated in various cosmetic products, such as cleansing water, oil-in-water emulsions, water-in-oil emulsions, oils, milks, lotions, shampoos, foaming products and sprays, whose compositions are presented below.

| Cleansing water for sensitive skin | |
|---|---|
| Brand or INCI name | % |
| Capryloyl glycine | 0-1% |
| Soda lye | 0-1% |
| Sequestrant | 0-1% |
| Butylene glycol | 1-5% |
| Beta-carotene | 0-2% |
| Polyphenol-rich avocado extract | 0.01-10% |
| Preservatives | 0-1% |
| PEG-32 | 1-5% |
| PEG-7 palmcocoate | 1-5% |
| Zinc gluconate | 0-1% |
| Citric acid | 0-1% |
| Purified water | q.s. to 100% |
| Fragrance | 0-1% |
| Poloxamer 184 | 1-5% |

| Anti-aging emulsion | |
|---|---|
| Brand or INCI name | % |
| Liquid isoparaffin | 5-20% |
| Isocetyl stearate | 5-20% |
| Al—Mg hydroxystearate | 5-20% |
| Abil WE 09 | 1-5% |
| Glycerol | 1-5% |
| Vaseline oil | 1-5% |
| Micronized zinc oxide | 1-5% |
| Butylene glycol | 1-5% |
| Retinol | 0-1% |
| Vitamin C | 0-5% |
| Polyphenol-rich avocado extract | 0.01-10% |
| Isononyl isononanoate | 1-5% |
| Beeswax | 1-5% |
| Sodium tartrate | 1-5% |
| Sodium chloride | 0-5% |
| Glycine | 1-5% |
| Preservatives | 0-1% |
| Cholesterol | 0-1% |
| Phytosphingosine | 0-1% |
| Tartaric acid | 0-1% |
| Purified water | q.s. to 100% |

| Milk for dry, atopic skin | |
|---|---|
| Raw material/Brand or INCI name | % |
| Sweet almond oil | 1-5% |
| Corn oil | 1-5% |
| Stearic acid | 1-5% |
| $C_{16}$-$C_{18}$ cetyl acid | 0-1% |
| Antifoam 70414 | 0-1% |
| Lauric alcohol 11OE | 1-5% |
| PEG 300 monolaurate | 0-1% |
| Glycerol monoleate | 0-1% |
| Glycerol monostearate | 1-5% |
| Vitamin B12 | 0-5% |
| Polyphenol-rich avocado extract | 0.1-10% |
| Preservatives | 0-1% |
| Citric acid | 0-1% |
| Trisodium citrate | 0-1% |
| Purified water | q.s. to 100% |
| Fragrance | 0-1% |
| Peanut oil | 1-5% |
| Hydrogenated palm oil | 1-5% |

| Cleansing cream | |
|---|---|
| Raw material/Brand or INCI name | % |
| Purified water | q.s. to 100% |
| Arlatone | 10-30% |
| Cocoglucoside | 5-20% |
| Hydroxypropyl guar | 1-5% |
| Capryloyl glycine | 0-2% |
| Preservatives | 0-2% |
| Fragrance | 0-1% |
| Citric acid | 0-1% |
| Zinc PCA | 0-1% |
| Polyphenol-rich avocado extract | 0.01-10% |

| Antidandruff shampoo | |
|---|---|
| Raw material/Brand or INCI name | % |
| Purified water | q.s. to 100% |
| Lauroamphoacetate | 5-20% |
| Cocoglucoside | 5-20% |
| PEG 6000 distearate | 1-5% |
| Preservatives | 0-2% |
| Vitamin F | 0-5% |
| Piroctone olamine | 0-2% |
| Polyphenol-rich avocado extract | 0.01-10% |
| Zinc pyrithione | 0-1% |
| pH adjuster | 0-1% |
| Sequestrant | 0-1% |
| Fragrance | 0-1% |

EXAMPLE 5: COMPOSITIONS FOR ORAL ADMINISTRATION

The avocado extracts are integrated into oral compositions, in compositions enabling the administration of 50 to 200 mg of polyphenol-rich avocado extract per day.

1/ Anti-Stretch Marks Composition in the Form of Soft Capsules

| | |
|---|---|
| Polyphenol-rich avocado extract | 30 mg |
| Awara oil | 60 mg |
| Unsaponifiable-rich rapeseed oil | 300 mg |
| Vitamin of group B (B1, B2, B3, B5, B6, B9, B12) | q.s. to 100% RDA |
| Tocotrienols | q.s. to 50% RDA |
| Vitamin E | |
| Beeswax | |
| Soy lecithin | |
| Alimentary gelatin | |
| Glycerin | q.s. to 1 soft capsule |

This composition is administered as four to six 500 mg capsules per day.

2/ Anti-Hair Loss Tablets

| | |
|---|---|
| Polyphenol-rich avocado extract | 25 mg |
| Cereal extracts (corn, buckwheat, millet, spelt) rich in sulfur amino acids | 200 mg |
| Vitamin C | q.s. to 50% RDA |
| Fish cartilage glycosaminoglycans | 200 mg |
| Glucidex IT 19 (compression agent) | q.s. to one 800 mg tablet |

This composition is administered as five to eight tablets per day.

3/ Example of Slimming Powder Sticks

| | |
|---|---|
| Polyphenol-rich avocado extract | 100 mg |
| Polyphenol-rich tea extract | 100 mg |
| OPC-rich grape extract | 50 mg |
| Plant beta-glucans | 100 mg |
| Xanthan gum | 1 mg |
| Sodium ascorbate | 0.3 mg |
| Maltodextrin | q.s. to 5 g |

This composition is administered twice per day.

EXAMPLE 6: BIOLOGICAL ACTIVITIES

1. Anti-Inflammatory Effect
a. Anti-Inflammatory Activity on Keratinocytes

In the skin, the keratinocyte is one of the first cells taking part in the initiation of the inflammatory reaction in response to attack by the environment.

The "attacked" keratinocyte then releases cytokines which induce a cascade of reactions involving the immune system.

✓ Materials and Methods:

Human keratinocytes (NCTC-2544 cell line) were preincubated or not (control) with the avocado extract concentrated in polyphenols (AV) at concentrations of 0.005% and 0.01% (w/v of active material) or the anti-inflammatory reference molecules ($10^{-7}$ M dexamethasone, $10^{-6}$ M indomethacin) for 24 hours. The cells were then treated with 0.1 µg/ml phorbol myristate acetate (PMA) for 24 hours, always in the presence of AV or the references.

At the end of the treatment, the quantities of interleukin 8 (IL8) and prostaglandin E2 (PGE2) secreted were measured by ELISA in the culture supernatants.

The results were analyzed statistically by a Student's t-test.

✓ Results and Conclusion:

AV strongly and significantly inhibited the production of the inflammatory mediators IL8 and PGE2 stimulated by PMA in keratinocytes (Table 1).

The AV extract thus has an anti-inflammatory activity.

TABLE 1

Production of IL8 and PGE2 by keratinocytes

| | IL8 (ng/ml) | Inhibition |
|---|---|---|
| Control cells | 0.1 ± 0.0 | |
| 0.1 µg/ml PMA | 50.1 ± 1.8 | |
| $10^{-7}$ M Dexamethasone | 7.4 ± 0.8 | 85% $p < 0.001$ |
| 0.005% AV | 24.2 ± 1.4 | 52% $p < 0.001$ |
| 0.01% AV | 13.7 ± 0.6 | 73% $p < 0.001$ |

| | PGE2 (ng/ml) | Inhibition |
|---|---|---|
| Control cells | 0.039 ± 0.0 | |
| 0.1 µg/ml PMA | 138.4 ± 10.6 | |
| $10^{-6}$ M Indomethacin | 0.039 ± 0.0 | 100% $p < 0.001$ |
| 0.005% AV | 32.3 ± 3.1 | 77% $p < 0.001$ |
| 0.01% AV | 10.1 ± 0.3 | 93% $p < 0.001$ | b. Inhibition of the Production of Leukotriene B4 by Neutrophils

Leukotriene B4 (LTB4) is a lipid inflammatory mediator arising from the arachidonic acid pathway.

LTB4 is produced and released in large quantities by human neutrophil granulocytes via the activation of the enzyme 5-lipoxygenase; it plays an essential role in the development of cutaneous inflammatory reactions.

✓ Materials and Methods:

Human neutrophils were preincubated for 15 minutes in the presence of the avocado extract concentrated in polyphenols (AV) at concentrations of 0.005%, 0.01% and 0.1% (w/v of active material).

The cells were then stimulated by adding 1 mg/ml opsonized zymosan.

After 10 minutes of incubation, the leukotriene B4 (LTB4) released by the cells was assayed in the cell supernatants by an ELISA technique.

The results were analyzed statistically by a Student's t-test.

✓ Results and Conclusion:

AV significantly inhibited the production of LTB4 induced by opsonized zymosan on neutrophils (Table 2).

Thus, the AV extract modulates the inflammation induced by the neutrophil and LTB4.

TABLE 2

Production of leukotriene B4 by neutrophils

| | LTB4 (pg/ml) | Inhibition |
|---|---|---|
| Control cells | 31 ± 2.8 | |
| Stimulated cells | 2900 ± 496.7 | |
| 0.005% AV | 2210 ± 779.3 | −24% ns |
| 0.01% AV | 1737.5 ± 197.4 | −40% $p < 0.01$ |
| 0.1% AV | 1925 ± 434.9 | −34% $p < 0.05$ |

C. Inhibition of Histamine Release

Mastocytes play an important role in allergic and inflammatory reactions. In human, they are widely distributed in connective tissue, such as the skin, serous mastocytes are the sentinel cells of the local inflammatory response. Substance P, a neuropeptide, acts on cutaneous mastocytes by inducing a rapid release of histamine preformed in storage granules; this mechanism of neurogenic inflammation is involved in various cutaneous pathologies.

✓ Materials and Methods:

Mastocytes were preincubated for 30 minutes in the presence of the avocado extract concentrated in polyphenols (AV) at a concentration of 0.01% (w/v of active material) or 10 mM calcium (reference inhibitor of histamine release).

The mastocytes were then stimulated with 10 µM substance P for 15 minutes. At the end of incubation, the release of histamine was quantified by ELISA.

The results were analyzed statistically by a Student's t-test.

✓ Results and Conclusion:

AV significantly inhibited the release of histamine by mastocytes stimulated with substance P (Table 3).

The AV extract modulates neurogenic inflammation notably related to histamine.

TABLE 3

Release of histamine by mastocytes

| | Histamine (ng/ml) | Inhibition |
|---|---|---|
| Control | 20.1 ± 1.9 | |
| Substance P | 142.5 ± 9.6 | |
| 10 nM Calcium | 21.8 ± 1.0 | −85% $p < 0.01$ |
| 0.01% AV | 112.5 ± 9.6 | −21% $p < 0.01$ |

2. Depigmenting Activity

The depigmenting effect of the AV extract was studied in two distinct models: by evaluation of the production of melanin in melanocytes; and by evaluation of the enzymatic activity of tyrosinase, a key enzyme involved in the synthesis of melanin.

a. Inhibition of Melanogenesis

✓ Materials and Methods:

Normal human epidermal melanocytes were cultured in the presence of $10^{-7}$ M NDP-MSH (α-MSH analog; induction of melanogenesis) and the avocado extract concentrated in polyphenols (AV) at concentrations of 0.001% and 0.005% (w/v of active material) or 0.25 mM kojic acid (reference).

After 240 hours of incubation, melanin was extracted from the cells and quantified by spectrophotometry.

The results were analyzed statistically by a Student's t-test.

✓ Results and Conclusion:

AV significantly inhibited the production of melanin by melanocytes stimulated by NDP-MSH (Table 4).

AV thus has a depigmenting effect.

TABLE 4

Melanin production by melanocytes

|  | Melanin (µl/ml) | |
|---|---|---|
| Control cells | 24.7 ± 0.0 | |
| Stimulated control (NDP-MSH) | 30.4 ± 0.9 | +19% p < 0.01 |
| Reference (kojic acid) | 9.6 ± 0.6 | −32% p < 0.001 |
| 0.001% AV | 26.2 ± 0.6 | −14% p < 0.05 |
| 0.005% AV | 25.7 ± 0.5 | −15% p < 0.05 | b. Inhibition of Tyrosinase Activity

✓ Materials and Methods:

The avocado extract concentrated in polyphenols (AV) and various concentrations of kojic acid (reference) were preincubated for 10 minutes at low temperature in the presence of tyrosinase extracted from human melanocytes.

The substrate of the enzyme, 2 mM T-DOPA, was then added.

After 1 hour of incubation at 37° C., enzymatic activity was evaluated by spectrophotometric measurement.

The results were analyzed statistically by a Student's t-test.

✓ Results and Conclusion:

AV significantly inhibited the enzymatic activity of tyrosinase (Table 5). This result confirms the depigmenting effect of this extract.

TABLE 5

Human tyrosinase activity

|  | Tyrosinase (U/ml) | Inhibition |
|---|---|---|
| Control | 182.7 | |
| 0.0625 mM Kojic acid | 166.8 | −9% p < 0.05 |
| 0.25 mM Kojic acid | 152.4 | −17% p < 0.001 |
| 0.001% AV | 165.5 | −9% p < 0.05 |
| 0.005% AV | 164.7 | −10% p < 0.05 |
| 0.01% AV | 162.5 | −11% p < 0.01 |
| 0.05% AV | 148.2 | −19% p < 0.001 |
| 0.1% AV | 142.4 | −22% p < 0.001 |

3. Healing Activity: Stimulation of Markers of reepithelialization

The cicatrization mechanism in response to a wound involves for epidermal repair a process of reepithelialization.

Cutaneous reepithelialization consists of the regeneration by keratinocytes of an organized, pavimentous, stratified and keratinized epithelium that covers the wound and that reconstitutes a protective barrier.

The reepithelialization mechanism proceeds in three steps: migration of keratinocytes, proliferation and maturation of the epidermis.

The effect of the AV extract was studied on the gene expression of markers involved in the keratinocyte migration step during this reepithelialization process, laminin-5 and matrix metalloproteinase-9 (MMP9).

✓ Materials and Methods:

Normal human keratinocytes were incubated for 48 hours in the presence of the avocado extract concentrated in polyphenols (AV) at concentrations of 0.001% and 0.005% (w/v of active material) or 5 ng/ml TGFβ1 (reference).

The gene expression of MMP9 and laminin-5 (subunit γ2) was studied by real-time RT-PCR.

The results were analyzed statistically by a one-factor ANOVA followed by a Dunnett's test: ns (not significant) p>0.05; *p<0.05; ***p<0.001.

✓ Results and Conclusion:

AV significantly increased the expression of markers of keratinocyte migration (Table 6).

This extract thus has a reepithelialization-activating effect, in favor of a repairing, pro-healing effect.

TABLE 6

Gene expression of markers for keratinocyte migration (relative quantity)

|  | Laminin-5 | | MMP9 | |
|---|---|---|---|---|
| Control cells | 1.00 | | 1.00 | |
| Reference (TGFβ1) | 11.33 | +1033% *** | 19.84 | +1884% *** |
| 0.001% AV | 1.62 | +62% * | 3.81 | +281% *** |
| 0.005% AV | 1.51 | +51% * | 9.17 | +817% *** |

The invention claimed is:

1. A method for preventing and/or treating allergic, inflammatory or irritative reactions of the skin and/or mucous membranes and/or appendages, or for preventing and/or treating disorders or pathologies of the skin barrier, or homeostasis of the skin, comprising administering to a subject in need thereof an effective amount of a cosmetic, pharmaceutical, dermatological, or nutraceutical composition comprising a polyphenol-rich extract of avocado fruit, comprising at least 10% polyphenols by weight, expressed in gallic acid equivalents in relation to the dry extract, and comprising 0 to 10% by weight of avocado lipids in relation to the dry extract, wherein the polyphenols comprise a mixture of procyanidins, caffeic acid and derivatives of caffeic acid, wherein the mixture is at least 70% by weight, expressed in gallic acid equivalents, in relation to total polyphenol content by weight, and wherein the mixture contains at least 20% caffeic acid and derivatives of caffeic acid and at least 30% procyanidins by weight, expressed in gallic acid equivalents, in relation to total polyphenol content by weight, wherein the extract further comprises at least 10% avocado sugars by weight in relation to the weight of the dry extract, said sugars containing at least D-mannoheptulose and/or perseitol, and wherein the extract further comprises 1 to 30% avocado proteins by weight in relation to the weight of the dry extract, and a suitable carrier.

2. A method for preventing and/or treating allergic, inflammatory or irritative reactions of the skin and/or mucous membranes and/or appendages, or for preventing and/or treating disorders or pathologies of the skin barrier, or homeostasis of the skin, comprising administering to a subject in need thereof an effective amount of a polyphenol-rich extract of avocado fruit, comprising at least 10% polyphenols by weight, expressed in gallic acid equivalents in relation to the dry extract, and comprising 0 to 10% by weight of avocado lipids in relation to the dry extract, wherein the polyphenols comprise a mixture of procyanidins, caffeic acid and derivatives of caffeic acid, wherein the mixture is at least 70% by weight, expressed in gallic acid equivalents, in relation to total polyphenol content by weight, and wherein the mixture contains at least 20% caffeic acid and derivatives of caffeic acid and at least 30% procyanidins by weight, expressed in gallic acid equivalents, in relation to total polyphenol content by weight, wherein said extract further comprises at least 10% avocado sugars by weight in relation to the weight of the dry extract, said sugars containing at least D-mannoheptulose and/or perseitol, and wherein said extract further comprises 1 to 30% avocado proteins by weight in relation to the weight of the dry extract.

3. A method for healing or depigmenting the skin and/or mucous membranes and/or appendages, comprising administering to a subject in need thereof an effective amount of a cosmetic, pharmaceutical, dermatological, or nutraceutical composition comprising a polyphenol-rich extract of avocado fruit, comprising at least 10% polyphenols by weight, expressed in gallic acid equivalents in relation to the dry extract, and comprising 0 to 10% by weight of avocado lipids in relation to the dry extract, wherein the polyphenols comprise a mixture of procyanidins, caffeic acid and derivatives of caffeic acid, wherein the mixture is at least 70% by weight, expressed in gallic acid equivalents, in relation to total polyphenol content by weight, and wherein the mixture contains at least 20% caffeic acid and derivatives of caffeic acid and at least 30% procyanidins by weight, expressed in gallic acid equivalents, in relation to total polyphenol content by weight, wherein said extract further comprises at least 10% avocado sugars by weight in relation to the weight of the dry extract, said sugars containing at least D-mannoheptulose and/or perseitol, and wherein said extract further comprises 1 to 30% avocado proteins by weight in relation to the weight of the dry extract, and a suitable carrier.

4. A method for healing or depigmenting the skin and/or mucous membranes and/or appendages, comprising administering to a subject in need thereof an effective amount of a polyphenol-rich extract of avocado fruit, comprising at least 10% polyphenols by weight, expressed in gallic acid equivalents in relation to the dry extract, and comprising 0 to 10% by weight of avocado lipids in relation to the dry extract, wherein the polyphenols comprise a mixture of procyanidins, caffeic acid and derivatives of caffeic acid, wherein the mixture is at least 70% by weight, expressed in gallic acid equivalents, in relation to total polyphenol content by weight, wherein the mixture contains at least 20% caffeic acid and derivatives of caffeic acid and at least 30% procyanidins by weight, expressed in gallic acid equivalents, in relation to total polyphenol content by weight, and wherein said extract further comprises at least 10% avocado sugars by weight in relation to the weight of the dry extract, said sugars containing at least D-mannoheptulose and/or perseitol, and wherein said extract further comprises 1 to 30% avocado proteins by weight in relation to the weight of the dry extract.

5. A method for preventing and/or treating vascular disorders, comprising administering to a subject in need thereof an effective amount of a cosmetic, pharmaceutical, dermatological, or nutraceutical composition comprising a polyphenol-rich extract of avocado fruit, comprising at least 10% polyphenols by weight, expressed in gallic acid equivalents in relation to the dry extract, and comprising 0 to 10% by weight of avocado lipids in relation to the dry extract, wherein the polyphenols comprise a mixture of procyanidins, caffeic acid and derivatives of caffeic acid, wherein the mixture is at least 70% by weight, expressed in gallic acid equivalents, in relation to total polyphenol content by weight, and wherein the mixture contains at least 20% caffeic acid and derivatives of caffeic acid and at least 30% procyanidins by weight, expressed in gallic acid equivalents, in relation to total polyphenol content by weight, and wherein said extract further comprises at least 10% avocado sugars by weight in relation to the weight of the dry extract, said sugars containing at least D-mannoheptulose and/or perseitol, and wherein said extract further comprises 1 to 30% avocado proteins by weight in relation to the weight of the dry extract, and a suitable carrier.

6. A method for preventing and/or treating vascular disorders, comprising administering to a subject in need thereof an effective amount of a polyphenol-rich extract of avocado fruit, comprising at least 10% polyphenols by weight, expressed in gallic acid equivalents in relation to the dry extract, and comprising 0 to 10% by weight of avocado lipids in relation to the dry extract, wherein the polyphenols comprise a mixture of procyanidins, caffeic acid and derivatives of caffeic acid, wherein the mixture is at least 70% by weight, expressed in gallic acid equivalents, in relation to total polyphenol content by weight, and wherein the mixture contains at least 20% caffeic acid and derivatives of caffeic acid and at least 30% procyanidins by weight, expressed in gallic acid equivalents, in relation to total polyphenol content by weight, and wherein said extract further comprises at least 10% avocado sugars by weight in relation to the weight of the dry extract, said sugars containing at least D-mannoheptulose and/or perseitol, and wherein said extract further comprises 1 to 30% avocado proteins by weight in relation to the weight of the dry extract.

7. A cosmetic care method for the skin and/or appendages and/or mucous membranes, for improving the condition and/or appearance of sensitive skin, or for preventing the accumulation of adipose tissue or skin with cellulitis, comprising administering to a subject in need thereof an effective amount of a cosmetic composition comprising a polyphenol-rich extract of avocado fruit, comprising at least 10% polyphenols by weight, expressed in gallic acid equivalents in relation to the dry extract, and comprising 0 to 10% by weight of avocado lipids in relation to the dry extract, wherein the polyphenols comprise a mixture of procyanidins, caffeic acid and derivatives of caffeic acid, wherein the mixture is at least 70% by weight, expressed in gallic acid equivalents, in relation to total polyphenol content by weight, and wherein the mixture contains at least 20% caffeic acid and derivatives of caffeic acid and at least 30% procyanidins by weight, expressed in gallic acid equivalents, in relation to total polyphenol content by weight, and wherein said extract further comprises at least 10% avocado sugars by weight in relation to the weight of the dry extract, said sugars containing at least D-mannoheptulose and/or perseitol, and wherein said extract further comprises 1 to 30% avocado proteins by weight in relation to the weight of the dry extract, and a suitable carrier.

8. A cosmetic care method for the skin and/or appendages and/or mucous membranes, for improving the condition and/or appearance of sensitive skin, or for preventing the accumulation of adipose tissue or skin with cellulitis, comprising administering to a subject in need thereof an effective amount of a polyphenol-rich extract of avocado fruit, comprising at least 10% polyphenols by weight, expressed in gallic acid equivalents in relation to the dry extract, and comprising 0 to 10% by weight of avocado lipids in relation to the dry extract, wherein the polyphenols comprise a mixture of procyanidins, caffeic acid and derivatives of caffeic acid, wherein the mixture is at least 70% by weight, expressed in gallic acid equivalents, in relation to total polyphenol content by weight, and wherein the mixture contains at least 20% caffeic acid and derivatives of caffeic acid and at least 30% procyanidins by weight, expressed in gallic acid equivalents, in relation to total polyphenol content by weight, and wherein said extract further comprises at least 10% avocado sugars by weight in relation to the weight of the dry extract, said sugars containing at least D-mannoheptulose and/or perseitol, and wherein said extract further comprises 1 to 30% avocado proteins by weight in relation to the weight of the dry extract.

9. A cosmetic care method for the skin and/or appendages and/or mucous membranes, for reducing pigmentation spots, comprising administering to a subject in need thereof an effective amount of a cosmetic composition comprising a polyphenol-rich extract of avocado fruit, comprising at least 10% polyphenols by weight, expressed in gallic acid equivalents in relation to the dry extract, and comprising 0 to 10% by weight of avocado lipids in relation to the dry extract, wherein the polyphenols comprise a mixture of procyanidins, caffeic acid and derivatives of caffeic acid, wherein the mixture is at least 70% by weight, expressed in gallic acid equivalents, in relation to total polyphenol content by weight, and wherein the mixture contains at least 20% caffeic acid and derivatives of caffeic acid and at least 30% procyanidins by weight, expressed in gallic acid equivalents, in relation to total polyphenol content by weight, and wherein said extract further comprises at least 10% avocado sugars by weight in relation to the weight of the dry extract, said sugars containing at least D-mannoheptulose and/or perseitol, and wherein said extract further comprises 1 to 30% avocado proteins by weight in relation to the weight of the dry extract, and a suitable carrier.

10. A cosmetic care method for the skin and/or appendages and/or mucous membranes, for reducing pigmentation spots, comprising administering to a subject in need thereof an effective amount of a polyphenol-rich extract of avocado fruit, comprising at least 10% polyphenols by weight, expressed in gallic acid equivalents in relation to the dry extract, and comprising 0 to 10% by weight of avocado lipids in relation to the dry extract, wherein the polyphenols comprise a mixture of procyanidins, caffeic acid and derivatives of caffeic acid, wherein the mixture is at least 70% by weight, expressed in gallic acid equivalents, in relation to total polyphenol content by weight, and wherein the mixture contains at least 20% caffeic acid and derivatives of caffeic acid and at least 30% procyanidins by weight, expressed in gallic acid equivalents, in relation to total polyphenol content by weight, and wherein said extract further comprises at least 10% avocado sugars by weight in relation to the weight of the dry extract, said sugars containing at least D-mannoheptulose and/or perseitol, and wherein said extract further comprises 1 to 30% avocado proteins by weight in relation to the weight of the dry extract.

11. A cosmetic care method for preventing and/or treating ageing of the skin and/or the appendages and/or the mucous membranes, comprising administering to a subject in need thereof an effective amount of a cosmetic composition comprising a polyphenol-rich extract of avocado fruit, comprising at least 10% polyphenols by weight, expressed in gallic acid equivalents in relation to the dry extract, and comprising 0 to 10% by weight of avocado lipids in relation to the dry extract, wherein the polyphenols comprise a mixture of procyanidins, caffeic acid and derivatives of caffeic acid, wherein the mixture is at least 70% by weight, expressed in gallic acid equivalents, in relation to total polyphenol content by weight, and wherein the mixture contains at least 20% caffeic acid and derivatives of caffeic acid and at least 30% procyanidins by weight, expressed in gallic acid equivalents, in relation to total polyphenol content by weight, and wherein said extract further comprises at least 10% avocado sugars by weight in relation to the weight of the dry extract, said sugars containing at least D-mannoheptulose and/or perseitol, and wherein said extract further comprises 1 to 30% avocado proteins by weight in relation to the weight of the dry extract, and a suitable carrier.

12. A cosmetic care method for preventing and/or treating ageing of the skin and/or the appendages and/or the mucous membranes, comprising administering to a subject in need thereof an effective amount of a polyphenol-rich extract of avocado fruit, comprising at least 10% polyphenols by weight, expressed in gallic acid equivalents in relation to the dry extract, and comprising 0 to 10% by weight of avocado lipids in relation to the dry extract, wherein the polyphenols comprise a mixture of procyanidins, caffeic acid and derivatives of caffeic acid, wherein the mixture is at least 70% by weight, expressed in gallic acid equivalents, in relation to total polyphenol content by weight, and wherein the mixture contains at least 20% caffeic acid and derivatives of caffeic acid and at least 30% procyanidins by weight, expressed in gallic acid equivalents, in relation to total polyphenol content by weight, and wherein said extract further comprises at least 10% avocado sugars by weight in relation to the weight of the dry extract, said sugars containing at least D-manno-heptulose and/or perseitol, and wherein said extract further comprises 1 to 30% avocado proteins by weight in relation to the weight of the dry extract.

* * * * *